United States Patent [19] [11] 4,136,124
Zinke-Allmang et al. [45] Jan. 23, 1979

[54] MANUFACTURE OF DIALKYL-KETALS

[75] Inventors: Helmut Zinke-Allmang, Bad Durkheim; Walter Scheidmeir, Limburgerhof, both of Fed. Rep. of Germany

[73] Assignee: BASF Aktiengesellschaft, Ludwigshafen, Fed. Rep. of Germany

[21] Appl. No.: 820,718

[22] Filed: Aug. 1, 1977

[30] Foreign Application Priority Data

Aug. 12, 1976 [DE] Fed. Rep. of Germany ....... 2636278

[51] Int. Cl.$^2$ ............................................. C07C 41/00
[52] U.S. Cl. ............................. 568/591; 260/340.5 R; 260/340.7; 568/592; 568/594

[58] Field of Search .......... 260/615 A, 611 R, 611 A, 260/340.5 R, 340.7

[56] References Cited

U.S. PATENT DOCUMENTS

| 2,110,499 | 3/1938 | Carothers | 260/615 A X |
| 2,374,494 | 4/1945 | Morey | 260/615 A |
| 2,451,949 | 10/1948 | Heinemann | 260/615 A |
| 2,519,540 | 8/1950 | Bramwyche et al. | 260/615 A |
| 2,827,494 | 3/1958 | Brown et al. | 260/615 A |

Primary Examiner—Howard T. Mars
Attorney, Agent, or Firm—Keil, Thompson & Shurtleff

[57] ABSTRACT

Dialkyl-ketals are manufactured by reacting ketones with alkanols in the presence of an acid condensing agent and of an at least equivalent amount, based on the ketone, of anhydrous calcium sulfate.

6 Claims, No Drawings

MANUFACTURE OF DIALKYL-KETALS

The present invention relates to an improved process for the manufacture of dialkyl-ketals by reacting ketones with alkanols in the presence of acid condensing agents.

Whilst dialkyl-acetals can in general be manufactured easily, and in high yields, from aldehydes and alkanols, the formally corresponding manufacture of ketals

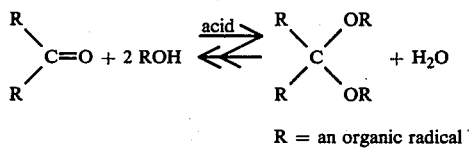

R = an organic radical

R = an organic radical presents substantial difficulties, because the equilibrium lies predominantly to the left-hand side of the equation. This follows from the research of Lorette et al in J. Org. Chem. (1959), 1,731–33 in which it is proposed to achieve the object of manufacturing ketals by reaction of a ketone and an alcohol by displacing the equilibrium, by means of strongly acid ion exchangers and low temperatures (about -28° C), in favor of ketal formation.

However, this process is not only inherently uneconomical because of the low temperatures but also because of the associated long reaction times and low degrees of conversion, which necessitate very involved working up by extraction and distillation.

It is an object of the present invention to provide a simpler method of manufacturing dialkyl-ketals.

We have found that this object is achieved and that dialkyl-ketals are obtained in an elegant manner and in high yields by reacting ketones with alkanols in the presence of an acid condensing agent, if the reaction is carried out in the presence of at least equivalent amounts, based on the ketone, of anhydrous calcium sulfate.

Since the calcium sulfate removes the water from the ketalization equilibrium by forming a hydrate, its use is advantageous regardless of the nature of the reactants and regardless of the reaction conditions. From a chemical point of view, it is therefore possible to use, as starting materials, any ketones

where $R^1$ and $R^2$ are aliphatic, araliphatic, aromatic or cycloaliphatic radicals, or radicals which are linked to one another to form a cycloaliphatic ring. From an industrial and economic point of view, the most important — at least at present — are the aliphatic ketones where $R^1$ and $R^2$ are alkyl of 1 to 4 carbon atoms, and amongst these especially acetone, methyl ethyl ketone and diethyl ketone. Cyclohexanone and acetophenone are also suitable.

Similar remarks apply to the alkanols. Since, as a rule, the ketones are ketalized in order to deactivate or protect the oxo group during organic syntheses or in the end products, it is preferred to use the cheap alkanols, e.g. methanol and ethanol, particularly since these are the most reactive. In general terms, alkanols of 1 to 12 carbon atoms are suitable, as are 1,2- and 1,3-alkanediols, since 5-membered and 6-membered cyclic ketals may also be manufactured by the process of the invention.

The ketone and the alkanol react with one another in the stoichiometric ratio but it is at times advantageous to employ more than 1 mole, e.g. up to about 4 moles, of alkanol per mole of ketone. The amount of calcium sulfate is preferably from 2.5 to 5 moles per mole of ketone. Larger amounts may also be used but as a rule produce no significant additional advantages.

Suitable acid condensing agents are, in general, strong mineral acids, e.g. hydrogen chloride and anhydrous sulfuric acid, and these are generally used in amounts of from 1 to 5 mmoles per mole of ketone. Solid acids, e.g. ion exchangers, are less suitable since they are difficult to separate from the calcium sulfate.

The ketalization is preferably carried out at room temperature, but in general terms temperatures from 15 to 80° C are suitable. Higher temperatures are less advisable, since at these temperatures the water is no longer as effectively bound by the calcium sulfate.

In a particularly advantageous embodiment of the process according to the invention, the reaction is carried out in the presence of substantial volumes, e.g. from about 0.5 to 2 liters per liter of the ketone/alkanol mixture, of a hydrocarbon or hydrocarbon mixture boiling at from 100 to 170° C at standard pressure; the boiling point should if possible differ by at least 10° C, but preferably by up to 60° C, from that of the ketal formed. Suitable hydrocarbons are, in the main, all paraffins which are liquid at room temperature, i.e. paraffins of 6 to 10 carbon atoms, e.g. hexane, octane and decane, as well as cyclohexane and also benzene, toluene, xylene and their mixtures.

The hydrocarbons offer the advantage that the ketal formed dissolves more easily therein, in contrast to the ketone or alkanol, and is thus, to a certain degree, withdrawn from the ketalization equilibrium. Furthermore, the calcium sulfate can be more easily suspended in the hydrocarbons than in the mixture of reactants. A particularly advantageous aspect is, however, that the calcium sulfate can, after completion of the reaction, i.e. when it has bound the water of reaction, readily be dehydrated again by heating in the hydrocarbon, the water being removed azeotropically. The fact that the dehydration of the calcium sulfate hydrate can be effected under such mild conditions should be singled out as a noteworthy feature.

Accordingly, an advantageous procedure is to stir a substantially anhydrous mixture of ketone, alkanol and acid with a suspension of the anhydrous calcium sulfate in a hydrocarbon which is higher-boiling than the ketal formed, at room temperature for from about 1 to 2 hours, then to remove the calcium sulfate from the mixture, distil off the ketone, alkanol and ketal from the hydrocarbon, suspend the hydrated calcium sulfate in the hydrocarbon and heat it until it has again been dehydrated, the suspension which remains being used for a fresh reaction batch. The azeotropes of ketone, alkanol and ketal which may in certain circumstances form on distillation can be split by the conventional methods or can, preferably, be recycled to a fresh ketalization batch. The main fraction obtained is as a rule the pure ketal in from about 85 to 98% yield. The process of the invention can also be carried out semi-continuously and completely continuously by employing the conventional techniques for this purpose.

The ketals are valuable intermediates for the manufacture of, for example, insecticides, herbicides and fungicides in which hydroxyl or amino groups present in the molecule can initially be protected by ketalizing, and which then only develop their action gradually, at the rate at which the ketone radical is split off under catalysis by, for example, acids, e.g. the humic acids in the soil. Ketalizing the hydroxyl groups may also serve to protect these groups during the snythesis. By trans-ketalizing lower ketals, e.g. dimethyl-ketals or diethyl-ketals, with higher alcohols or diols, the corresponding higher or cyclic ketals can easily be manufactured and this method is frequently simpler than directly ketaliz-ing with the higher alcohols. The ketals, above all 2,2-dimethoxypropane, also serve as dehydrating agents for sensitive organic compounds.

EXAMPLE 1

670 g (11.5 moles) of acetone, 740 g (23 moles) of methanol and 40 mg (about 1 mole) of hydrogen chloride were stirred for one hour at room temperature with a suspension of 5.5 kg of decane and 4.1 kg (about 30 moles) of anhydrous calcium sulfate. Working up the liquid phase by distillation gave 150 g of an azeotrope of 8 g of 2,2-dimethoxypropane, 30 g of acetone and 112 g of methanol, 177 g of an azeotrope of 83 g of the ketal and 94 g of methanol, and 910 g of 2,2-dimethoxypropane of 99% purity.

Accordingly, in the last fraction the desired ketal was obtained in about 87% yield. The calcium sulfate was subsequently re-dehydrated by heating in the decane.

EXAMPLES 2 to 4

Using the method described in Example 1, acetone and ethanol or propan-1-ol or butan-1-ol were used to manufacture the corresponding ketals, namely 2,2-diethoxypropane in 95% yield, 2,2-di-1-propoxypropane in 90% yield and 2,2-di-1-butoxypropane in 90% yield.

We claim:

1. In a process for the manufacture of a dialkylketal by reacting a ketone with an alkanol in the presence of an acid condensing agent, wherein the improvement comprises:

carrying out the reaction in the presence of at least an equivalent amount, based on the ketone, of anhydrous calcium sulfate and in the presence of from 0.5 to 2 liters of a hydrocarbon or hydrocarbon mixture per liter of the ketone/alkanol mixture.

2. A process set forth in claim 1, wherein from 2.5 to 5 moles of anhydrous calcium sulfate are used per mole of ketone.

3. A process as set forth in claim 1, wherein the reaction is carried out at temperatures of from 15 to 80° C.

4. A process as set forth in claim 1, wherein hydrocarbon or hydrocarbon mixture boils at from 100 to 170° C.

5. A process as set forth in claim 1, wherein the hydrocarbons are paraffins of 6 to 10 carbon atoms, cyclohexane, and benzene, toluene, xylene and their mixtures.

6. A process as set forth in claim 1, wherein the boiling point of the hydrocarbon is at least 10° C different from that of the ketal formed.

* * * * *